(12) United States Patent
Greif et al.

(10) Patent No.: US 6,569,881 B1
(45) Date of Patent: May 27, 2003

(54) SUBSTITUTED BENZIMIDAZOLE, THE PRODUCTION THEREOF AND THE USE THEREOF AS MEANS AGAINST PARASITIC PROTOZOA

(75) Inventors: Giesela Greif, Remagen (DE); Axel Haberkorn, Wuppertal (DE); Bernd Baasner, Gladbach (DE); Folker Lieb, Leverkusen (DE); Albrecht Marhold, Leverkusen (DE); Jörn Stölting, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/018,212

(22) PCT Filed: Apr. 26, 2000

(86) PCT No.: PCT/EP00/03714

§ 371 (c)(1), (2), (4) Date: Oct. 30, 2001

(87) PCT Pub. No.: WO00/68225

PCT Pub. Date: Nov. 16, 2000

(30) Foreign Application Priority Data

May 5, 1999 (DE) ......................................... 199 20 551

(51) Int. Cl.$^7$ ..................... A01N 43/52; C07D 405/06; A61K 31/415
(52) U.S. Cl. .................................... 514/394; 548/304.7
(58) Field of Search ....................... 548/304.7; 514/394

(56) References Cited

U.S. PATENT DOCUMENTS

| 3,418,318 | A | 12/1968 | Lambie et al. ........... 260/247.5 |
| 3,472,865 | A | 10/1969 | Tattersall et al. ......... 260/309.2 |
| 4,434,173 | A | 2/1984 | Welch, Jr. .................... 424/271 |
| 4,448,732 | A | 5/1984 | Welch, Jr. ................. 260/245.2 |
| 4,536,502 | A | 8/1985 | Giraudon et al. ............ 514/227 |
| 4,622,323 | A | 11/1986 | Giraudon et al. ........... 514/228 |
| 4,859,684 | A | 8/1989 | Raeymaekers et al. ..... 514/314 |
| 5,331,003 | A | 7/1994 | O'Doherty .................. 514/394 |
| 5,482,956 | A | * | 1/1996 | Lunkenheimer et al. .... 514/394 |

FOREIGN PATENT DOCUMENTS

| DE | 20 47 369 | 4/1971 |
| DE | 42 37 617 | 5/1994 |
| EP | 0039477 | * 11/1981 |
| EP | 0 181 826 | 5/1986 |
| EP | 0 239 508 | 9/1987 |

OTHER PUBLICATIONS

**Patent Abstracts of Japan, vol. 007, No. 273 (C–198), Dec. 6, 1983 (Dec. 6, 1983) & JP 58 152879 A (Mitsubishi Kasei Kogyo KK), Sep. 10, 1983 (Sep. 10, 1983) in der Anmeldung erwähnt Zusammenfassung.

**H. Dvorakova: Collection of Czechoslovak Ckhemical Communications, Bd. 53, Nr.*, 1988, Seiten 1779–94, XP000925891 Seite 1780, Schema I, Verbindungen II, III und IV, Seite 1788, Zeile 26 — Zeile 45 Seite 1789, Zeile 34 —Seite 1790, Zeile 10.

* cited by examiner

Primary Examiner—Cecilia Tsang
Assistant Examiner—Andrea D. Small
(74) Attorney, Agent, or Firm—Susan M. Pellegrino

(57) ABSTRACT

The present invention relates to a new substituted benzimidazoles, their preparation and their use as agents against parasitic protozoa.

6 Claims, No Drawings

SUBSTITUTED BENZIMIDAZOLE, THE PRODUCTION THEREOF AND THE USE THEREOF AS MEANS AGAINST PARASITIC PROTOZOA

This application is a 371 of PCT/EP00/03714.

The present invention relates to new substituted benzimidazoles, their preparation and their use as agents against parasitic protozoa.

The present invention further relates to mixtures of these compounds with polyether antibiotics or synthetically prepared coccidiosis agents in compositions for controlling parasitic protozoa, in particular coccidia.

Substituted benzimidazoles and their use as insecticides, fungicides and herbicides have already been disclosed (EP-OS(European Published Specification) 87 375, 152 360, 181 826, 239 508, 260 744, 266 984, U.S. Pat. Nos. 3,418,318, 3,472,865, 3,576,818, 3,728,994.

Halogenated benzimidazoles and their action as anthelmintics, coccidiostatics and pesticides have been disclosed (DE-OS(German Published Specification) 2 047 369, DE-OS (German Published Specification) 4 237 617). Mixtures of nitro-substituted benzimidazoles and polyether antibiotics have been disclosed as coccidiosis agents (U.S. Pat. No. 5,331,003). In all cases, their action is still not satisfactory.

Coccidiosis is a disease which is caused by single-celled parasites (protozoa). In particular in poultry breeding, it can cause great losses. In order to avoid these, the populations are treated prophylactically with coccidiosis agents. Owing to the development of resistance to the agents employed, serious problems occur even shortly after introduction of the agents. By means of the use of coccidiosis agents which are chemically completely new, in particular combinations, it is also possible, on the other hand, to control polyresistant parasite strains.

New benzimidazoles of the formula (I)

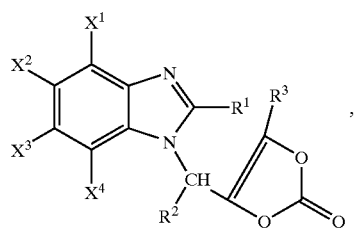

(I)

in which
$R^1$ represents fluoroalkyl,
$R^2$ represents hydrogen or alkyl,
$R^3$ represents alkyl,
$X^1$, $X^2$, $X^3$ and $X^4$ independently of one another represent hydrogen, halogen, halogenoalkyl, halogenoalkoxy, halogenoalkylthio or halogenoalkylsulfonyl,
or alternatively
$X^2$ and $X^3$ or $X^3$ and $X^4$ together represent a dioxyhaloalkylene, have been found, which exhibit outstanding activity against coccidiosis.

The benzimidazoles of the formula (I)

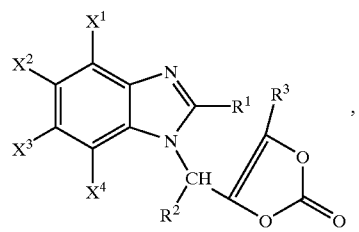

(I)

in which
$R^1$, $R^2$, $R^3$, $X^1$ to $X^4$ have the abovementioned meanings, are prepared by
reacting 1 H-benzimidazoles of the formula (II)

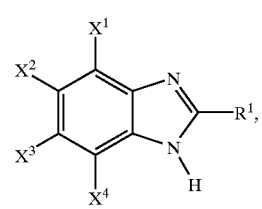

(II)

in which
$R^1$ and $X^1$ to $X^4$ have the meaning indicated above, with an alkylating agent of the formula (III)

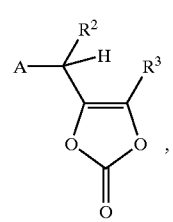

(III)

in which
A represents a suitable leaving group,
$R^2$ and $R^3$ have the meaning indicated above, if appropriate in the presence of diluents and/or reaction auxiliaries.

Depending on the type and number of the substituents, the compounds of the formula (I) can optionally be present as geometrical and/or optical isomers or regioisomers or isomer mixtures thereof in varying composition. Both the pure isomers and the isomer mixtures are claimed according to the invention.

Formula (I) provides a general definition of the substituted benzimidazoles according to the invention. Preferred compounds of the formula (I) are those in which
$R^1$ represents $C_1$–$C_4$-fluoroalkyl,
$R^2$ represents hydrogen or $C_1$–$C_4$-alkyl,
$R^3$ represents $C_1$–$C_4$-alkyl,
$X^1$, $X^2$, $X^3$ and $X^4$ independently of one another represent hydrogen, F, Cl, Br, $C_1$–$C_4$-halogenoalkyl, $C_1$–$C_4$-halogenoalkoxy, $C_1$–$C_4$-halogenoalkylthio, $C_1$–$C_4$-halogenoalkylsulfonyl,
$X^2$ and $X^3$ or $X^3$ and $X^4$ can also together represent a dioxyhalo-$C_1$–$C_4$-alkylene radical.

Particularly preferred compounds of the formula (I) are those in which $R^1$ represents $CF_3$, $CHF_2$, CHF, $R^2$ represents hydrogen, methyl, ethyl, n-propyl or isopropyl, $R^3$ represents methyl, ethyl, n-propyl or isopropyl, $X^1$, $X^2$, $X^3$ and $X^4$ independently of one another represent hydrogen, F, Cl, Br, $CF_3$, $CHF_2$, $CH_2F$, $OCF_3$, $OCH_2F$, $OCHF_2$, $SCF_3$, $SCHF_2$, $SCH_2F$, $SO_2CF_3$, $SO_2CHF_2$, $SO_2CH_2F$, where $X^2$ and $X^3$ or $X^3$ and $X^4$ can also together represent a radical —O—$CF_2$—O—, —O—$CF_2$—$CF_2$—O—, —O—$CF_2$—$CF_2$—$CF_2$—O—, —O—$CF_2$—CHF—O—, —O—CClF—CClF—O—, —O—CHF—O—, —O—CHF—CHF—O— or —O—CClF—O—.

Very particularly preferred compounds of the formula (I) are those in which $R^1$ represents —$CF_3$ or —$CHF_2$, $R^2$ represents hydrogen, $R^3$ represents methyl, $X^1$ represents hydrogen, —$CF_3$, Cl, Br, F or —$SCF_3$, $X^2$ represents hydrogen, —$OCF_3$, F, Br, Cl or $CF_3$, $X^3$ represents F, Br, Cl, —$OCF_3$, —$CF_3$ or —$SO_2CF_3$, $X^4$ represents hydrogen, where $X^2$ and $X^3$ or $X^3$ and $X^4$ can also represent —$OCF_2$—CFHO—, —O—CClF—CClF—O—, —$OCF_2$—$CF_2$—O— or —O—$CF_2$—O—.

If, for carrying out the process according to the invention for the preparation of compounds of the formula (I), 4-bromo-2,6-bis-trifluoromethylbenzimidazole, for example, is used, the course of the reaction of the preparation process can be represented by the following equation:

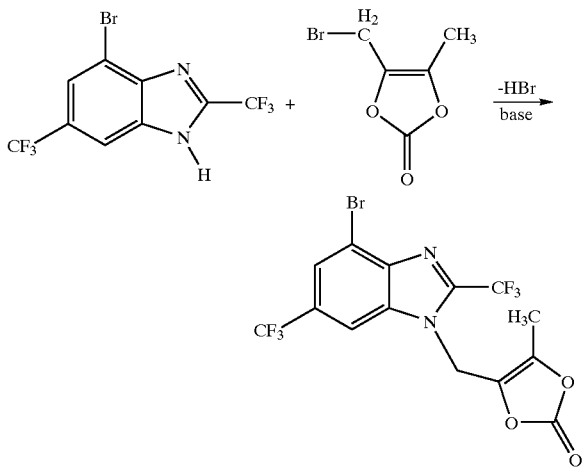

Formula (II) provides a general definition of the 1H-benzimidazoles needed as starting substances for carrying out the preparation process. In this formula (II), $R^1$ to $R^3$ and $X^1$ to $X^4$ preferably represent those radicals which have already been mentioned as preferred for these substituents in connection with the description of the compounds of the formula (I) according to the invention.

The 1H-benzimidazoles of the formula (II) are known or obtainable in analogy to known processes (cf., for example, J. Amer. Chem. Soc. 75, 1292 [1953] U.S. Pat. No. 3.576.818).

Formula (III) provides a general definition of the alkylating agents furthermore necessary as starting materials for carrying out the preparation process. In this formula (III), $R^2$ and $R^3$ preferably represent those radicals which have already been mentioned as preferred for these substituents in connection with the description of the substances of the formula (I) according to the invention.

A represents a leaving radical which is customary in alkylating agents, preferably halogen, in particular chlorine, bromine or iodine, or in each case optionally substituted alkylsulfonyloxy, alkoxysulfonyloxy or arylsulfonyloxy, such as, in particular, methanesulfonyloxy, trifluoromethanesulfonyloxy, methoxysulfonyloxy, ethoxysulfonyloxy or p-toluenesulfonyloxy.

The compounds of the formula (III) are generally known or obtainable in analogy to known processes (cf., for example, JP 58152879 [CA 100: 121042]; U.S. Pat. Nos. 4,434,173; 4,448,732).

Suitable diluents for carrying out the preparation process are inert organic solvents. These in particular include aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobultyl ketone; nitriles, such as acetonitrile, propionitrile or benzonitrile; amides, such as N,N-dimethylformamide, N,N-dimethylacetamide, N-methylformanilide, N-methylpyrrolidone or hexamethyl phosphoramide; esters, such as methyl acetate or ethyl acetate or bases such as pyridine or organic acids, such as formic acid or acetic acid.

The preparation process is preferably carried out in the presence of a suitable reaction auxiliary. Those suitable are all customary inorganic or organic bases. These include, for example, alkaline earth metal or alkali metal hydrides, hydroxides, amides, alkoxides, acetates, carbonates or hydrogencarbonates, such as, for example, sodium hydride, sodium amide, lithium diethylamide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogencarbonate, sodium hydrogencarbonate or ammonium carbonate, organolithium compounds, such as n-butyllithium, and tertiary amines, such as trimethylamine, triethylamine, tributylamine, di-isopropyl-ethylamine, tetramethylguanidine, N,N-dimethylaniline, pyridine, piperidine, N-methylpiperidine, N,N-dimethylaminopyridine, diazabicyclo octane (DABCO), diazabicyclononene (DBN) or diazabicycloundecene (DBU).

The preparation process can optionally also be carried out in a two-phase system, such as, for example, water/toluene or water/dichloromethane, if appropriate in the presence of a suitable phase-transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyl-dimethyl-ammonium methylsulfate, dimethyl-$C_{12}/C_{14}$-alkyl-benzylammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxy-ethoxy)-ethyl]-amine.

When carrying out the preparation process, the reaction temperatures can be varied within a relatively wide range. In general, the reaction is carried out at temperatures between −70° C. and +200° C., preferably at temperatures between 0° C. and 130° C.

The preparation process is customarily carried out under atmospheric pressure. However, it is also possible to work at elevated or reduced pressure.

To carry out the preparation process, in general 1.0 to 5.0 mol, preferably 1.0 to 2.5 mol, of alkylating agent of the formula (III) and, if appropriate, 0.01 to 5.0 mol, preferably 1.0 to 3.0 mol, of reaction auxiliary are employed per mole of 1H-benzimidazole of the formula (II).

The reaction is carried out and worked up and the reaction products are isolated according to known processes (for this cf. also the preparation examples).

The final products of the formula (I) are purified with the aid of customary processes, for example by column chromatography or by recrystallization.

Characterization is carried out with the aid of the melting point or, in the case of non-crystallizing compounds—in particular in the case of regioisomer mixtures—, with the aid of proton nuclear magnetic resonance spectroscopy [$^1$H-NMR].

The active compounds are suitable for controlling parasitic protozoa which occur in animal keeping and animal breeding with agricultural animals, breeding animals, zoo animals, laboratory animals, experimental animals and pets and have favorable toxicity to warm-blooded animals. In this context, they are active against all or individual stages of development of the pests and against resistant and normally sensitive strains. By means of the control of the parasitic protozoa, disease, cases of death and yield reductions (e.g. in the production of meat, milk, wool, hides, eggs, honey etc.) should be decreased, so that more economical and simpler animal keeping is possible by the use of the active compounds.

The parasitic protozoa include: Mastigophora (Flagellata) such as, for example, Trypanosomatidae e.g. *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae e.g. *Giardia lamblia, G. canis*.

Sarcomastigophora (Rhizopoda) such as Entamoebidae, for example, *Entamoeba histolytica*, Hartmanellidae, for example, Acanthamoeba sp., Hartmanella sp.

Apicomplexa (Sporozoa) such as Eimeridae, for example, *Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra*, E. spec., *E. stiedai, E. suis, E. tenella, E. truncata, E. truttae, E. zuernii*, Globidium spec., *Hammon dia heyderni, Isospora belli, I. canis, I. felis, I. ohioensis, I. rivolta*, I. spec., *I. suis*, Neospora spec., *Neospora carinum, Neospora hugesi, Neospora caninum*, Cystisospora spec, Crypiosporidium spec. such as Toxoplasmadidae, for example, *Toxoplasma gondii*, such as Sarcocystidae, for example, *Sarcocystis bovicanis, S. bovihominis, S. neurona, S. ovicanis, S. ovifelis*, S. spec., S. suihominis such as Leucozoidae, for example, *Leucozytozoon simondi*, such as Plasmodiidae, for example, *Plasmodium berghei, P. falciparum, P. malariae, P. ovale, P. vivax*, P. spec., such as Piroplasmea, for example, *Babesia argentina, B. bovis, B. canis*, B. spec., *Theileria parva*, Theileria spec., such as Adeleina, for example, *Hepatozoon canis*, H. spec.

Furthermore Myxospora and Microspora, for example, Glugea spec. Nosema spec.

Furthermore *Pneumocystis carinii*, and also Ciliophora (Ciliata) such as, for example, *Balantidium coli*, Ichthiophthirius spec., Trichodina spec., Epistylis spec.

The compounds according to the invention are also active against protozoa which occur as parasites in insects. Those which may be mentioned are parasites of the strain Microsporida, in particular of the genus Nosema. *Nosema apis* in the honey bee may be particularly mentioned.

The agricultural and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, pigeons, species of birds for keeping in homes and zoos. Productive and ornamental fish are furthermore included.

Laboratory and experimental animals include mice, rats, guinea pigs, golden hamsters, dogs and cats.

The pets include dogs and cats.

The fish include productive, breeding, aquarium and ornamental fish of all age levels, which live in fresh and salt water. The productive and breeding fish include, for example, carp, eel, trout, whitefish, salmon, bream, roach, rudd, chub, sole, plaice, halibut, Japanese yellowtail (*Seriola quinqueradiata*), Japanese eel (*Anguilla japonica*), red seabream (*Pagurus major*), seabass (*Dicentrarchus labrax*), grey mullet (*Mugilus cephalus*), pompano, gilthread seabream (*Sparus auratus*), Tilapia spp., Chichlidae species such as, for example, plagioscion, channel catfish. The compositions according to the invention are particularly suitable for the treatment of fry, e.g. carp of 2 to 4 cm body length. The compositions are also very highly suitable in eel feeding.

Administration can be carried out either prophylactically or therapeutically.

The active compounds are administered directly or enterally, parenterally, dermally, nasally in the form of suitable preparations.

Enteral administration of the active compounds is carried out, for example, orally in the form of powders, suppositories, tablets, capsules, pastes, drinks, granules, drenches, boluses, medicated feed or drinking water. Dermal administration is carried out, for example, in the form of dipping, spraying, bathing, washing, pouring on and spotting on and of powdering. Parenteral administration takes place, for example, in the form of injection (intramuscular, subcutaneous, intravenous, intraperitoneal) or by means of implants.

Suitable preparations are:
Solutions such as injection solutions, oral solutions, concentrates for oral administration after dilution, solutions for use on the skin or in body cavities, pour-on formulations, gels;
emulsions and suspensions for oral or dermal administration and also for injection; semi-solid preparations;
formulations in which the active compound is processed in an ointment base or in an oil-in-water or water-in-oil emulsion base;
solid preparations such as powders, premixes or concentrates, granules, pellets, tablets, boluses, capsules; aerosols and inhalants, active compound-containing molded articles.

Injection solutions are administered intravenously, intramuscularly and subcutaneously.

Injection solutions are prepared by dissolving the active compound in a suitable solvent and adding possible additives such as solubilizers, acids, bases, buffer salts, antioxidants, preservatives. The solutions are sterile filtered and bottled.

Solvents which may be mentioned are: physiologically tolerable solvents such as water, alcohols such as ethanol, butanol, benzyl alcohol, glycerol, hydrocarbons, propylene glycol, polyethylene glycols, N-methylpyrrolidone, and mixtures thereof.

The active compounds can optionally also be dissolved in physiologically tolerable vegetable or synthetic oils which are suitable for injection.

Solubilizers which may be mentioned are: solvents which promote the dissolution of the active compound in the main solvent or prevent its precipitation. Examples are polyvinylpyrrolidone, polyoxyethylated castor oil, polyoxyethylated sorbitan ester.

Preservatives are: benzyl alcohol, trichilorobutanol, p-hydroxybenzoic acid esters, n-butanol.

Oral solutions are administered directly. Concentrates are administered orally after prior dilution to the use concentration. Oral solutions and concentrates are prepared as described above in the case of the injection solutions, it being possible to dispense with working under sterile conditions.

Solutions for use on the skin are trickled on, smoothed on, rubbed in, sprinkled on, sprayed on or applied by dipping, bathing or washing. These solutions are prepared as described above in the case of the injection solutions.

It may be advantageous to add thickeners during the preparation. Thickeners are: inorganic thickeners such as bentonites, colloidal silicic acid, aluminum monostearate, organic thickeners such as cellulose derivatives, polyvinyl alcohols and their copolymers, acrylates and metacrylates.

Gels are applied or painted onto the [lacuna] or introduced into body cavities. Gels are prepared by mixing solutions, which have been prepared as described in the case of the injection solutions, with sufficient thickener such that a clear material having an ointment-like consistency results. The thickeners employed are the thickeners indicated further above.

Pour-on formulations are poured or sprinkled onto restricted areas of the skin, the active compound either penetrating the skin and acting systemically or being distributed on the body surface.

Pour-on formulations are prepared by dissolving, suspending or emulsifying the active compound in suitable skin-compatible solvents or solvent mixtures. If appropriate, further auxiliaries such as colorants, absorption-promoting substances, antioxidants, light screens, tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone, 2-dimethyl-4-oxy-methylene-1,3-dioxolane.

Colorants are all colorants, which can be dissolved or suspended, permitted for use in animals.

Absorption-promoting substances are, for example, DMSO, spreading oils such as isopropyl myristate, dipropylene glycol pelargonate, silicone oils, fatty acid esters, triglycerides, fatty alcohols.

Antioxidants are sulfites or metabisulfites such as potassium metabisulfite, ascorbic acid, butylhydroxytoluene, butylhydroxyanisole, tocopherol.

Light screens are, for example, substance from the benzophenones class or novantisolic acid.

Tackifiers are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, further auxiliaries such as colorants, absorption-promoting substances, preservatives, antioxidants, light screens, viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid biglyceride, triglyceride mixture with plant fatty acids of chain length $C_{8-12}$ or other specially selected natural fatty acids, partial glyceride mixtures of saturated or unsaturated fatty acids possibly also containing hydroxyl groups, mono- and diglycerides of the $C_8/C_{10}$ fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}-C_{18}$, isopropyl myristate, isopropyl palmitate, caprylic/capric acid esters of saturated fatty alcohols of chain length $C_{12}-C_{18}$, isopropyl stearate, oleyl oleate, decyl oleate, ethyl oleate, ethyl lactate, waxy fatty acid esters such as dibutyl phthalate, diisopropyl adipate, ester mixtures related to the last-mentioned, inter alia fatty alcohols such as isotridecyl alcohol, 2-octyl dodecanol, cetylstearyl alcohol, oleyl alcohol.

Fatty acids such as, for example, oleic acid and its mixtures.

Hydrophilic phases which may be mentioned are: water, alcohols such as, for example, propylene glycol, glycerol, sorbitol and their mixtures.

Emulsifiers which may be mentioned are:

nonionic surfactants, e.g. polyoxyethylated castor oil, polyoxyethylated sorbitan monooleate, sorbitan monostearate, glyceryl monostearate, polyoxyethyl stearate, alkylphenol polyglycol ether;

ampholytic surfactants such as di-Na N-lauryl-β-iminodipropionate or lecithin;

anionic surfactants, such as Na laurylsulfate, fatty alcohol ether sulfates, mono/dialkyl polyglycol ether orthophosphoric acid ester monoethanolamine salt; cationic surfactants such as cetyltrimethylammonium chloride.

Further auxiliaries which may be mentioned are:

Substances increasing viscosity and stabilizing the emulsion such as carboxymethyl-cellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally, dermally or as an injection. They are prepared by suspending the active compound in a carrier liquid, if appropriate with addition of further auxiliaries such as wetting agents, colorants, absorption-promoting substances, preservatives, antioxidants, light screens.

Carrier liquids which may be mentioned are all homogeneous solvents and solvent mixtures.

Wetting agents (dispersants) which may be mentioned are the surfactants indicated further above.

Further auxiliaries which may be mentioned are those indicated further above.

Semi-solid preparations can be administered orally or dermally. They differ from the suspensions and emulsions described above only by their higher viscosity.

For the production of solid preparations, the active compound is mixed with suitable carriers, if appropriate with addition of auxiliaries, and brought into the desired form.

Carriers which may be mentioned are all physiologically tolerable solid inert substances. All those used are inorganic and organic substances. Inorganic substances are, for example, sodium chloride, carbonates such as calcium carbonate, hydrogen carbonates, aluminum oxides, silicic acids, argillaceous earths, precipitated or colloidal silica, phosphates.

Organic substances are, for example, sugar, cellulose, foodstuffs and feedstuffs such as milk powder, animal meal, cereal meals and coarse cereal meals, starches.

Auxiliaries are preservatives, antioxidants, colorants which have already been mentioned further above.

Further suitable auxiliaries are lubricants and glidants such as, for example, magnesium stearate, stearic acid, talc, bentonites, disintegration-promoting substances such as starch or crosslinked polyvinylpyrrolidone, binders such as, for example, starch, gelatin or linear polyvinylpyrrolidone, and dry binders such as microcrystalline cellulose.

The active compounds can also be present in the preparations as a mixture with synergists or with other active compounds.

Mixtures of the compounds according to the invention with a polyether antibiotic or a synthetically prepared coccidiosis agent may be particularly emphasized.

Synthetic coccidiosis agents or polyether antibiotics for use in the mixtures according to the invention which may preferably be mentioned are:

Amprolium, in some cases in combination with folic acid antagonists

Robenidine

Toltrazuril

Monensin

Salinomycin

Maduramicin

Lasalocid

Narasin

Semduramicin.

The mixture with maduramicin may particularly be emphasized.

Ready-to-use preparations contain the active compounds in concentrations of 10 ppm to 20 percent by weight, preferably of 0.1 to 10 percent by weight.

Preparations which are diluted before use contain the active compound in concentrations of 0.5 to 90 percent by weight, preferably of 1 to 50 percent by weight.

In general, it has proven advantageous to administer amounts of approximately 0.5 to approximately 50 mg, preferably 1 to 20 mg, of active compound per kg of body weight per day to achieve effective results.

In the mixture with other coccidiosis agents or polyether antibiotics, the active compounds according to the invention are present in the ratio 1 to 0.1–10 to 1 to 1–10. The ratio 1 to 5 is preferred.

The active compounds can also be administered together with the feed or drinking water of the animals.

Feedstuffs and foodstuffs contain 0.01 to 250 ppm, preferably 0.5 to 100 ppm, of the active compound in combination with a suitable edible material.

Such a feedstuff and foodstuff can be used both for curative purposes and for prophylactic purposes.

Such a feedstuff or foodstuff is prepared by mixing a concentrate or a premixture, which contains 0.5 to 30%, preferably 1 to 20%, by weight of an active compound mixed with an edible organic or inorganic carrier, with customary feedstuffs. Edible carriers are, for example, corn meal or corn and soybean meal or mineral salts, which preferably contain a small amount of an edible dust prevention oil, e.g. corn oil or soybean oil. The premixture obtained here can then be added to the complete feedstuff before feeding it to the animals.

Use in coccidiosis may be mentioned by way of example:

For the curing and propylaxis, for example, of coccidiosis in poultry, in particular in chickens, ducks, geese and turkeys, 0.1 to 100 ppm, preferably 0.5 to 100 ppm, of an active compound are mixed with a suitable edible material, e.g. a nutritious feedstuff. If desired, these amounts can be increased, particularly if the active compound is well tolerated by the recipient. Accordingly, administration can be carried out via the drinking water.

For the treatment of individual animals, e.g. in the case of the treatment of coccidiosis in mammals or of toxoplasmosis, amounts of active compound of 0.5 to 100 mg/kg of body weight daily are preferably administered in order to achieve the desired results. In spite of this, it can periodically be necessary to deviate from the amounts mentioned, in particular depending on the body weight of the experimental animal or on the type of administration method, but also because of the animal genus and its individual reaction to the active compound or the manner of formulation and the time or the interval at which it is administered. Thus, in certain cases it may suffice to manage with less than the abovementioned minimum amount, while in other cases the upper limit mentioned has to be exceeded. In the case of the administration of relatively large amounts, it may be expedient to divide these into a number of individual administrations over the course of the day.

The efficacy of the compounds according to the invention can be confirmed, for example, in cage experiments using the following experimental arrangement, in which the animals are treated with the respective individual components and with the mixtures of the individual components.

An active compound-containing feed is prepared in such a way that the required amount of active compound is thoroughly mixed with a nutritionally balanced animal feed, e.g. with the chick feed indicated below.

If a concentrate or a premix is to be prepared, which is finally to be diluted in the feed to the values mentioned in the experiment, in general approximately 1 to 30%, preferably approximately 10 to 20%, by weight of active compound are mixed with an edible organic or inorganic carrier, e.g. corn meal and soybean meal or mineral salts which contain a small amount of an edible anti-dust oil, e.g. corn oil or soybean oil. The premix thus obtained can then be added to the complete poultry feed before administration.

A suitable example of the use of the substances according to the invention in poultry feed is the following composition.

52.00% of coarse feed cereal meal, namely: 40% corn, 12% wheat
17.00% of coarse soybean meal extr.
5.00% of corn gluten feed
5.00% of wheat feed meal
3.00% of fish meal
3.00% of mineral mixture
3.00% of alfalfa meal
2.50% of vitamin premix
2.00% of wheatgerms, comminuted
2.00% of soybean oil
2.00% of meat and bonemeal
1.50% of whey powder
1.00% of molasses
1.00% of brewer's yeast, bound to brewer's grains 100.00%

Such a feed contains 18% of raw protein, 5% of raw fiber, 1% of Ca, 0.7% of P and, per kg, 1200 IU of vitamin A, 1200 IU of vitamin D3, 10 mg of vitamin E, 20 mg of zinc bacitracin.

PREPARATION EXAMPLES COMPOUNDS OF THE FORMULA (I)

Example 1

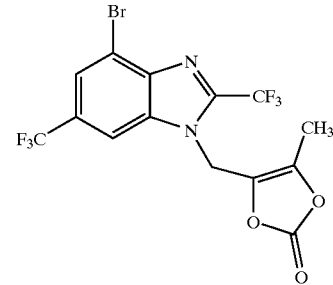

3.3 g (10 mmol) of 4-bromo-2,6-bis-trifluoromethylbenzimidazole are introduced into 100 ml of methylene chloride and 1.73 ml (12.5 mmol) of triethylamine are added at 20° C. 2.4 g (12.5 mmol) of 4-bromomethyl-5-methyl-1,3-dioxol-2-one in 10 ml of methylene chloride are then added dropwise and the mixture is refluxed for 24 h. The methylene chloride solution is washed 3 times with 30 ml of water each time, dried over sodium sulfate and concentrated in vacuo. The residue is chromatographed on silica gel (35–70 µm) using cyclohexane/ethyl acetate (3:1). 1.5 g (34% of theory) of the above compound are obtained. M.p.: 141–143° C.

Examples 2 to 28 were obtained analogously to Example 1 and according to the general details for preparation.

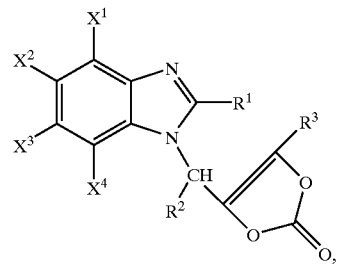

| Example | $X_1$ | $X_2$ | $X_3$ | $X_4$ | $R_1$ | $R_2$ | $R_3$ | M.p. [° C.] |
|---|---|---|---|---|---|---|---|---|
| 2 | H | —OCF$_2$—CFHO— | | H | CF$_3$ | H | CH$_3$ | 141–143 |
| 3 | H | —OCF$_2$—CFHO— | | H | CHF$_2$ | H | CH$_3$ | 65–70 |
| 4 | H | CF$_3$O | Br | H | CF$_3$ | H | CH$_3$ | 170–172 |
| 5 | H | CF$_3$O | Cl | H | CF$_3$ | H | CH$_3$ | 167–169 |
| 6 | CF$_3$ | H | Cl | H | CF$_3$ | H | CH$_3$ | 152–154 |
| 7 | H | —OCClF—CClFO— | | H | CF$_3$ | H | CH$_3$ | 113–115 |
| 8 | H | —OCF$_2$—CHFO— | | H | CF$_3$ | H | CH$_3$ | 150–152 |
| 9 | H | Br | CF$_3$O | H | CF$_3$ | H | CH$_3$ | 160–162 |
| 10 | H | Cl | CF$_3$O | H | CF$_3$ | H | CH$_3$ | 151–153 |
| 11 | Cl | H | CF$_3$ | H | CF$_3$ | H | CH$_3$ | 108–110 |
| 12 | CF$_3$ | H | Br | H | CF$_3$ | H | CH$_3$ | 147–149 |
| 13 | H | CF$_3$ | CF$_3$ | H | CF$_3$ | H | CH$_3$ | 167–169 |
| 14 | Br | H | —OCF$_2$—CF$_2$O— | | CF$_3$ | H | CH$_3$ | 182–184 |
| 15 | Cl | H | —OCF$_2$—CF$_2$O— | | CF$_3$ | H | CH$_3$ | 196–197 |
| 16 | H | —OCF$_2$—CF$_2$O— | | H | CF$_3$ | H | CH$_3$ | 160–162 |
| 17 | H | —OCF$_2$O— | | H | CF$_3$ | H | CH$_3$ | 106–109 |
| 18 | H | Cl | CF$_3$ | H | CF$_3$ | H | CH$_3$ | 177–179 |
| 19 | H | CF$_3$ | Cl | H | CF$_3$ | H | CH$_3$ | 152–153 |
| 20 | H | CF$_3$ | Br | H | CF$_3$ | H | CH$_3$ | 148–150 |
| 21 | F | H | CF$_3$ | H | CF$_3$ | H | CH$_3$ | 134–136 |
| 22 | CF$_3$ | H | F | H | CF$_3$ | H | CH$_3$ | 97.5–100.5 |
| 23 | SCF$_3$ | H | Br | H | CF$_3$ | H | CH$_3$ | Oil |
| 24 | F | Cl | F | H | CF$_3$ | H | CH$_3$ | Oil |
| 25 | Br | H | SO$_2$CF$_3$ | H | CF$_3$ | H | CH$_3$ | Oil |
| 26 | Cl | H | SO$_2$CF$_3$ | H | CF$_3$ | H | CH$_3$ | Oil |

-continued

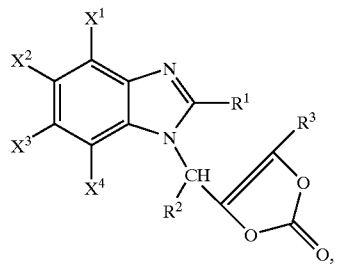

| Example | $X_1$ | $X_2$ | $X_3$ | $X_4$ | $R_1$ | $R_2$ | $R_3$ | M.p. [° C.] |
|---|---|---|---|---|---|---|---|---|
| 27 | H | —OCF$_2$—CF$_2$O— | | H | CF$_3$ | H | CH$_3$ | Oil |
| 28 | CF$_3$ | H | CF$_3$ | H | CF$_3$ | H | CH$_3$ | 101–103 |
| 29 | H | CF$_3$ | OCF$_3$ | H | CF$_3$ | H | CH$_3$ | 150–151 |
|  | H | OCF$_3$ | CF$_3$ | H | CF$_3$ | H | CH$_3$ |  |
| 30 | CF$_3$ | H | OCF$_3$ | H | CF$_3$ | H | CH$_3$ | Oil |

PREPARATION OF THE STARTING COMPOUND FOR EXAMPLE 14

Example a)

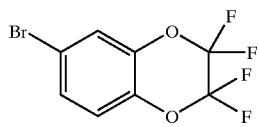

1400 g (6.7 mol) of 2,3-tetrafluoro-1,4-benzodioxane and 7 g (0.08 mol) of FeS (powder) are introduced, 1190 g (7.4 mol) of bromine are added dropwise at 20 to 30° C. in the course of about 4 h and the mixture is stirred for about 20 h until the evolution of gas is complete. It is washed with aqueous sodium sulfite solution and dried over sodium sulfate. The residue is distilled in vacuo.

Yield: 1540 g (80% of theory), b.p. 10: 70–74° C. (GC: 99%).

Example b)

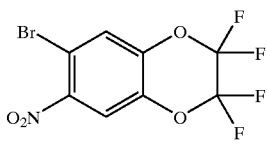

350 g (1.2 mol) of 6-bromo-2,3-tetrafluoro-1,4-benzodioxane are added dropwise at 20° C. in the course of 75 min to 273 ml of (98% strength) nitric acid and 293 ml of conc. sulfuric acid and the mixture is stirred for 1 h at 20° C. and 3 h at 40° C. The batch is poured onto ice, extracted with methylene chloride, and the organic phase is washed with water and with aqueous sodium hydrogencarbonate solution and dried over sodium sulfate. The organic phase is evaporated and reacted further as a crude product.

Yield: 396 g (98% of theory), (crude, GC: 99.1%), b.p.16: 121–124° C., nD: 1.5065 at 20° C.

Example c)

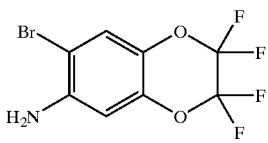

396 g (1.2 mol) of 6-bromo-7-nitro-2,3-tetrafluoro-1,4-benzodioxane are introduced into 1400 ml of ethanol, 253 g (4.5 mol) of Fe powder are added and the mixture is heated to reflux. 29 g of conc. hydrochloric acid are then added dropwise under reflux and the mixture is stirred for 1 h, 43 ml of water are added dropwise at boiling heat and the mixture is stirred for 2 h. The batch is cooled, and the precipitate is filtered off with suction and washed with ethanol. The mother liquor is rendered alkaline and evaporated. The residue is taken up in methylene chloride and washed twice with water and dried over sodium sulfate. The organic phase is evaporated.

Yield: 313 g (87% of theory), (GC: 95.3%).

Example d)

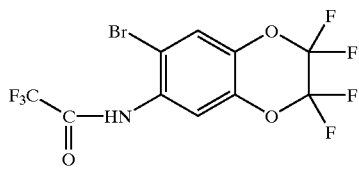

313 g (1.04 mol) of 7-amino-6-bromo-2,3-tetrafluoro-1,4-benzodioxane are introduced into 1250 ml of toluene and 500 g (4.4 mol) of trifluoroacetic acid and 188 g (1.3 mol) of phosphorous pentoxide are added in portions at 20 to 25° C. The batch becomes lumpy. It is heated for 1 h at 80° C. (not stirrable). The mixture is treated with 500 ml of water and stirred for 1 h at 80° C. After cooling, the organic phase is separated off and dried over sodium sulfate. The evaporated residue (340 g) still contains 50% of starting material (GC).

The residue (340 g, 50% pure), is therefore treated again with 1250 ml of toluene and 500 g (4.4 mol) of trifluoroacetic acid, then 188 g (1.3 mol) of phosphorus pentoxide are added in portions and the mixture is heated at 80° C. for 5 h. The organic phase is decanted off, washed twice with water, dried over sodium sulfate and evaporated.

Yield: 273 g (66% of theory), m.p.: 79–81° C. (GC: 98%)

The lumpy reaction residue is treated with water, and the organic component is separated off, dried over sodium sulfate and evaporated.

Yield: 56 g (14%), (GC 87%).

Example e)

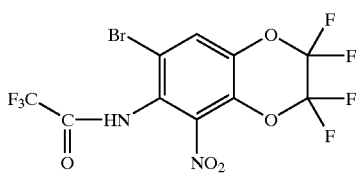

273 g (0.7 mol) of 6-bromo-7-trifluoromethylcarbonylamino-2,3-tetrafluoro-1,4-benzodioxane are introduced into 2047 ml of conc. sulfuric acid and 300 g of mixed acids are added dropwise at 0° C. in the course of 15 min and the thick magma is treated at 0 to 20° C. with 100 ml of methylene chloride. The solution is then stirred at 40° C. for 2 h. The cooled contents of the flask are poured onto ice water and the precipitate is isolated. The organic phase is separated off from the mother liquor and dried over sodium sulfate. The evaporated residue and the isolated precipitate are combined.

Yield: 269 g (88% of theory), m.p.: 158–159° C. (GC: 100%).

Example f)

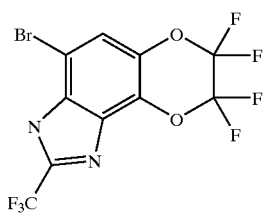

347 g (0.8 mol) of 6-bromo-8-nitro-7-trifluoromethylcarbonylamino-2,3-tetrafluoro -1,4-benzodioxane are introduced into 1735 ml of ethanol and 183 g (3.3 mol) of Fe turnings and 183 g (3.3 mol) of Fe powder are added. 38.5 ml of hydrochloric acid are added dropwise under reflux, the mixture is stirred for 1 h, then 58 ml of water are added dropwise and the mixture is refluxed for 15 h. The cooled batch is filtered off with suction, and the mother liquor is rendered alkaline and evaporated. The residue is taken up in methylene chloride, washed twice with water, dried over sodium sulfate and evaporated. The residue (170 g) is chromatographed on 1 kg of silica gel (35–70 μm) using cyclohexane/ethyl acetate (5:1).

Yield: 125 g (40% of theory), m.p. 162–164° C.

Biological Examples

Cape Experiments Coccidiosis/Chicks 8 to 12 day-old male chicken chicks raised under coccidea-free conditions (e.g. LSL Brinkschulte/Senden) receive the compounds according to the invention (test substances) from 3 days before (day -3) the infection (=a.i.) until 8 (9) days after the infection (=p.i.) with the feed in the concentration indicated in ppm. Three animals are kept in each cage. Per dose, one to a number of groups of this type are employed. Infection is carried out by means of a stomach tube directly into the crop using approximately 100,000 sporulated oocysts of *Eimeria acervulina* and with in each case approximately 30,000 oocysts of *E. maxima* and 40,000 sporulated oocysts of *E. tenella*. These are highly virulent strains. The exact infectious dose is adjusted such that if possible one of three experimentally infected untreated chicks dies due to infection. For the assessment of the efficacy, the following criteria are taken into consideration: weight increase from the start of the experiment to the end of the experiment, death rate due to infection, macroscopic assessment of the faeces with respect to diarrhoea and excretion of blood on days 5 and 7 p.i. (grade 0 to 6), macroscopic grade of the intestinal mucous membrane, in particular of the cecums (grade 0 to 6) and the oocyst excretion and also the proportion (in %) of the oocysts sporulating within 24 hours. The number of oocysts in the faeces was determined with the aid of the McMaster counting chamber (see Engelbrecht and coworkers "Parasitologische Arbeitsmethoden in Medizin und Veterinärmedizin, [Parasitological working methods in medicine and veterinary medicine] Akademie-Verlag, Berlin (1965)). The individual findings are related to the untreated noninfected control groups and an overall grade is calculated (cf. A. Haberkorn (1986), pp. 263 to 270 in Research in Avian Coccidiosis ed L. R. McDougald, L. P. Joyner, P. L. Long Proceedings of the Georgia Coccidiosis Conference Nov, 18–20, 1985 Athens/Ga. USA).

Experimental results using combinations according to the invention are shown by way of example in the following tables. The synergistic activity of the combinations in comparison with the individual components is particularly evident in the reduction of the oocyst secretion but also with respect to the secion findings, weight development and better tolerability.

In the following tables, the information in the column "treatment" means n.inf.contr.=noninfected control group inf.contr.=infected control group 1=Benzimidazole Example No.

In the column "ppm", the concentration of the active compound employed in the feed is indicated in ppm.

In the column "mortality", the percentage of the animals which have died is indicated under % and the number of the animals which have died/animals employed in the experiment is indicated under n.

In the column "weight % of not inf. control", the ratio of the weight of the treated animals to the weight of the noninfected control group is indicated.

In the columns "dropping scores", "lesion score" and "oocyst control", individual details of the action are given.

In the column "% efficacy", the overall rating is assessed; 0% means no action, 100% means complete action.

The results of the efficacy experiments using the compounds according to the invention are summarized in the following table:

TABLE 1

Efficacy against *Eimeria acervulina*, *Eimeria maxima*, and *Eimeria tenella*

| Compound | Dose in ppm | | |
|---|---|---|---|
| | 25 | 10 | 5 |
| Ex. 13 | D D D | 2 2 2 | 2 1 1 |
| Ex. 14 | D/2 | 2 2 1 | 2 2 1 |
| Ex. 15 | 2 2 1 | 2 1 2 | 1 0 1 |
| Ex. 28 | D/2 | 2 2 2 | 2 2 2 |
| Ex. 18 | 2 1 2 | 0 0 0 | 0 0 0 |

TABLE 1-continued

Efficacy against *Eimeria acervulina*, *Eimeria maxima*, and *Eimeria tenella*

| Compound | Dose in ppm | | |
|---|---|---|---|
| | 25 | 10 | 5 |
| Ex. 11 | 2 2 2 | 1 1 1 | 0 0 0 |
| Ex. 19 | 0 0 0 | 2 1 1 | 0 0 0 |

Grading scheme:
2 = complete action
1 = weak action
0 = inactive
D = death

TABLE 2

Experimental infection with *Eimeria acervulina*, *Eimeria maxima* and *Eimeria tenella* in chicks.
Example 13

| Treatment | | mortality | | weight % of not inf. control | dropping scores | lesion score | oocyst in % of inf. control | | | | % efficacy |
|---|---|---|---|---|---|---|---|---|---|---|---|
| | ppm | % | n | | | | ac. | max. | ten. | tot. | tot. |
| n. inf. contr. | 0 | 0 | 0/6 | 100 | 0 | 0 | 0 | 0 | 0 | 0 | 100 |
| inf. contr. | 0 | 78 | 7/9 | 25 | 6 | 6 | 100 | 100 | 100 | 100 | 0 |
| | 10 | 0 | 0/3 | 83 | 6 | 4.3 | 0 | 0 | 0 | 0 | 73 |
| | 5 | 33 | 1/3 | 74 | 6 | 6 | 5 | 0 | 3 | 4 | 50 |
| | 2.5 | 33 | 1/3 | 61 | 6 | 6 | 55 | 0 | 27 | 41 | 15 |

TABLE 3

Experimental infection with *Eimeria acervulina*, *Eimeria maxima* and *Eimeria tenella* in chicks.
Example 14

| Treatment | | mortality | | weight % of not inf. control | dropping scores | lesion score | oocyst in % of inf. control | | | | % efficacy |
|---|---|---|---|---|---|---|---|---|---|---|---|
| | ppm | % | n | | | | ac. | max. | ten. | tot. | tot. |
| n. inf. contr. | 0 | 0 | 0/6 | 100 | 0 | 0 | 0 | 0 | 0 | 0 | 100 |
| inf. contr. | 0 | 42 | 5/12 | 30.5 | 6 | 6 | 100 | 100 | 100 | 100 | 0 |
| | 10 | 0 | 0/3 | 81 | 4 | 6 | 1 | 0 | 7 | 4 | 69 |
| | 5 | 33 | 1/3 | 90.6 | 6 | 5.5 | 3 | 6 | 1 | 2 | 66 |
| | 2.5 | 0 | 0/3 | 44 | 6 | 6 | 92 | 0 | 12 | 35 | 30 |

TABLE 4

Experimental infection with *Eimeria acervulina*, *Eimeria maxima* and *Eimeria tenella* in chicks.
Example 15

| Treatment | mortality | | | weight % of not inf. control | dropping scores | lesion score | oocyst in % of inf. control | | | | % efficacy tot. |
|---|---|---|---|---|---|---|---|---|---|---|---|
| | ppm | % | n | | | | ac. | max. | ten. | tot. | |
| n. inf. contr. | 0 | 0 | 0/6 | 100 | 0 | 0 | 0 | 0 | 0 | 0 | 100 |
| inf. contr. | 0 | 50 | 6/12 | 18 | 6 | 6 | 100 | 100 | 100 | 100 | 0 |
| | 25 | 100 | 3/3 | D | 0 | D | D | D | D | D | D |
| | 10 | 0 | 0/3 | 82 | 0 | 0 | 0 | 0 | 0 | 0 | 91 |
| | 5 | 0 | 0/3 | 85 | 6 | 1 | 2 | 2 | 0 | 1 | 75 |

TABLE 5

Experimental infection with *Eimeria acervulina*, *Eimeria maxima* and *Eimeria tenella* in chicks.
Example 28

| Treatment | mortality | | | weight % of not inf. control | dropping scores | lesion score | oocyst in % of inf. control | | | | % efficacy tot. |
|---|---|---|---|---|---|---|---|---|---|---|---|
| | ppm | % | n | | | | ac. | max. | ten. | tot. | |
| n. inf. contr. | 0 | 0 | 0/6 | 100 | 0 | 0 | 0 | 0 | 0 | 0 | 100 |
| inf. contr. | 0 | 50 | 6/12 | 18 | 6 | 6 | 100 | 100 | 100 | 100 | 0 |
| | 25 | 100 | 3/3 | D | 0 | D | D | D | D | D | D |
| | 10 | 0 | 0/3 | 82 | 0 | 0 | 0 | 0 | 0 | 0 | 91 |
| | 5 | 0 | 0/3 | 85 | 6 | 1 | 2 | 2 | 0 | 1 | 75 |

TABLE 6

Experimental infection with *Eimeria acervulina*, *Eimeria maxima* and *Eimeria tenella* in chicks.
Example 18

| Treatment | mortality | | | weight % of not inf. control | dropping scores | lesion score | oocyst in % of inf. control | | | | % efficacy tot. |
|---|---|---|---|---|---|---|---|---|---|---|---|
| | ppm | % | n | | | | ac. | max. | ten. | tot. | |
| n. inf. contr. | 0 | 0 | 0/6 | 100 | 0 | 0 | 0 | 0 | 0 | 0 | 100 |
| inf. contr. | 0 | 17 | 2/12 | 32 | 6 | 6 | 100 | 100 | 100 | 100 | 0 |
| | 25 | 0 | 0/3 | 82 | 1 | 3 | 0 | 20 | 1 | 1 | 75 |
| | 10 | 0 | 0/3 | 30 | 6 | 6 | >100 | 0 | >100 | >100 | 5 |
| | 5 | 0 | 0/3 | 33 | 6 | 6 | >100 | >100 | >100 | >100 | 7 |

TABLE 7

Experimental infection with *Eimeria acervulina*, *Eimeria maxima* and *Eimeria tenella* in chicks.
Example 11

| Treatment | mortality | | | weight % of not inf. control | dropping scores | lesion score | oocyst in % of inf. control | | | | % efficacy tot. |
|---|---|---|---|---|---|---|---|---|---|---|---|
| | ppm | % | n | | | | ac. | max. | ten. | tot. | |
| n. inf. contr. | 0 | 0 | 0/6 | 100 | 0 | 0 | 0 | 0 | 0 | 0 | 100 |

TABLE 7-continued

Experimental infection with *Eimeria acervulina*, *Eimeria maxima* and *Eimeria tenella* in chicks.
Example 11

| Treatment | ppm | mortality % | mortality n | weight % of not inf. control | dropping scores | lesion score | oocyst in % of inf. control ac. | max. | ten. | tot. | % efficacy tot. |
|---|---|---|---|---|---|---|---|---|---|---|---|
| inf. contr. | 0 | 78 | 7/9 | 6 | 6 | 6 | 100 | 100 | 100 | 100 | 0 |
|  | 25 | 0 | 0/3 | 67 | 2 | 0 | 0 | 0 | 0 | 0 | 79 |
|  | 0 | 0 | 0/3 | 52 | 6 | 6 | 38 | 0 | 27 | 34 | 39 |
|  | 5 | 66 | 2/3 | 17 | 6 | 6 | >100 | 0 | >100 | >100 | 0 |

TABLE 8

Experimental infection with *Eimeria acervulina*, *Eimeria maxima* and *Eimeria tenella* in chicks.
Example 19

| Treatment | ppm | mortality % | mortality n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 17 | 1/6 | 53 | 6 | 6 | 100 | 100 | 100 | 100 | 0 |
|  | 25 | 0 | 0/3 | 56 | 6 | 6 | >100 | >100 | >100 | >100 | 7 |
|  | 10 | 0 | 0/3 | 75 | 3 | 4 | 5 | 13 | 5 | 5 | 66 |
|  | 5 | 0 | 0/3 | 52 | 4 | 6 | >100 | >100 | >100 | >100 | 7 |

TABLE 9

Combination examples
Experimental infection with *Eimeria acervulina*, *Eimeria maxima* and *Eimeria tenella* in chicks.
Ex. 15 in combination with Maduramicin.

| Treatment | ppm | mortality % | mortality n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 0 | 0/6 | 58 | 6 | 6 | 100 | 100 | 100 | 100 | 0 |
| MAD | 1 | 0 | 0/3 | 77 | 0 | 5 | 60 | 0 | 19 | 31 | 38 |
| MAD | 2 | 0 | 0/3 | 74 | 0 | 3 | 13 | 0 | 4 | 7 | 55 |
| MAD | 3 | 0 | 0/3 | 76 | 0 | 1 | 17 | 0 | 23 | 21 | 61 |
| Ex. 15 | 2.5 | 0 | 0/3 | 80 | 1 | 6 | 48 | 0 | 48 | 48 | 43 |
| Ex. 15 | 5 | 0 | 0/3 | 75 | 6 | 6 | 49 | 0 | 23 | 31 | 23 |
| Ex. 15 | 7.5 | 0 | 0/3 | >100 | 6 | 2 | 16 | 0 | 12 | 13 | 60 |
| Ex. 15 | 10 | 0 | 0/3 | 92 | 0 | 1 | 2 | 0 | 1 | 1 | 89 |
| Ex. 15 + MAD | 2.5 + 1 | 0 | 0/3 | >100 | 0 | 0 | 3 | 0 | 28 | 22 | 83 |
| Ex. 15 + MAD | 5 + 1 | 0 | 0/3 | >100 | 0 | 0 | 0 | 0 | 1 | 1 | 100 |
| Ex. 15 + MAD | 7.5 + 1 | 0 | 0/3 | >100 | 0 | 0 | 0 | 0 | 0 | 0 | 100 |
| Ex. 15 + MAD | 10 + 1 | 0 | 0/3 | 97 | 0 | 0 | 0 | 0 | 0 | 0 | 100 |
| Ex. 15 + MAD | 2.5 + 2 | 0 | 0/3 | 93 | 0 | 0 | 3 | 0 | 13 | 10 | 86 |

TABLE 9-continued

Combination examples
Experimental infection with *Eimeria acervulina*, *Eimeria maxima* and *Eimeria tenella* in chicks.
Ex. 15 in combination with Maduramicin.

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| Ex. 15 + MAD | 5 + 2 | 0 | 0/3 | 94 | 0 | 0 | 3 | 0 | 2 | 2 | 92 |
| Ex. 15 + MAD | 7.5 + 2 | 0 | 0/3 | >100 | 0 | 0 | 1 | 0 | 0.5 | 0.7 | 95 |
| Ex. 15 + MAD | 10 + 2 | 0 | 0/3 | >100 | 0 | 0 | 0 | 0 | 0 | 0 | 100 |
| Ex. 15 + MAD | 2.5 + 3 | 0 | 0/3 | 97 | 0 | 0 | 4 | 0 | 2 | 3 | 92 |
| Ex. 15 + MAD | 5 + 3 | 0 | 0/3 | 95 | 0 | 0 | 2 | 0 | 0 | 0.8 | 95 |
| Ex. 15 + MAD | 7.5 + 3 | 0 | 0/3 | >100 | 0 | 0 | 1 | 0 | 0 | 0 | 95 |
| Ex. 15 + MAD | 10 + 3 | 66 | 0/3 | 94 | 0 | 0 | 0 | 0 | 0 | 0 | 100 |

TABLE 10

Experimental infection with *Eimeria acervulina*, *Eimeria maxima* and *Eimeria tenella* in chicks.
Ex. 13 in combination with Maduramicin.

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 33 | 2/6 | 42 | 6 | 6 | 100 | 100 | 100 | 100 | 0 |
| MAD | 1 | 0 | 0/3 | 56 | 6 | 6 | >100 | 18 | >100 | >100 | 38 |
| MAD | 2 | 0 | 0/3 | 60 | 6 | 6 | 39 | 27 | 22 | 33 | 32 |
| MAD | 3 | 33 | 1/3 | 92 | 0 | 1 | 0 | 0 | 0 | 0 | 93 |
| Ex. 13 | 2.5 | 0 | 0/3 | 61 | 6 | 6 | 33 | 55 | >100 | 57 | 16 |
| Ex. 13 | 5 | 0 | 0/3 | 74 | 6 | 4.6 | 25 | 36 | 27 | 26 | 32 |
| Ex. 13 | 7.5 | 0 | 0/3 | 81 | 6 | 5.3 | 0 | 0 | 0 | 0 | 74 |
| Ex. 13 | 10 | 0 | 0/3 | 76 | 6 | 5.3 | 0 | 0 | 0 | 0 | 78 |
| Ex. 13 + MAD | 5 + 1 | 0 | 0/3 | 91 | 0 | 3 | 0 | 0 | 0 | 0 | 95 |
| Ex. 13 + MAD | 7.5 + 1 | 0 | 0/3 | 78 | 0 | 1 | 0 | 0 | 0 | 0 | 89 |
| Ex. 13 + MAD | 10 + 1 | 0 | 0/3 | 68 | 6 | 1 | 0 | 0 | 0 | 0 | 74 |
| Ex. 13 + MAD | 2.5 + 2 | 0 | 0/3 | 90 | 0 | 3 | 0 | 0 | 0 | 0 | 95 |
| Ex. 13 + MAD | 5 + 2 | 0 | 0/3 | 82 | 0 | 0.7 | 0 | 0 | 0 | 0 | 89 |
| Ex. 13 + MAD | 7.5 + 2 | 0 | 0/3 | 93 | 0 | 1 | 0 | 0 | 0 | 0 | 98 |

TABLE 10-continued

Experimental infection with *Eimeria acervulina*, *Eimeria maxima* and *Eimeria tenella* in chicks.
Ex. 13 in combination with Maduramicin.

| Treat-ment | ppm | mortality % | mortality n | weight % of not inf. control | drop-ping scores | lesion score | oocyst in % of inf. control ac. | max. | ten. | tot. | % effi-cay tot. |
|---|---|---|---|---|---|---|---|---|---|---|---|
| Ex. 13 + MAD | 10 + 2 | 0 | 0/3 | 72 | 0 | 3 | 0 | 0 | 0 | 0 | 77 |
| Ex. 13 + MAD | 5 + 3 | 0 | 0/3 | 69 | 0 | 0.7 | 0 | 0 | 0 | 0 | 80 |
| Ex. 13 + MAD | 7.5 + 3 | 0 | 0/3 | 79 | 0 | 0 | 0 | 0 | 0 | 0 | 91 |
| Ex. 13 + MAD | 10 + 3 | 66 | 0/3 | 76 | 0 | 0 | 0 | 0 | 0 | 0 | 91 |

TABLE 11

Experimental infection with *Eimeria acervulina*, *Eimeria maxima* and *Eimeria tenella* in chicks.
Ex. 14 in combination with Maduramicin.

| Treat-ment | ppm | mortality % | mortality n | weight % of not inf. control | drop-ping scores | lesion score | oocyst in % of inf. control ac. | max. | ten. | tot. | % effi-cay tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 0 | 0/6 | 55 | 6 | 6 | 100 | 100 | 100 | 100 | 0 |
| MAD | 1 | 0 | 0/3 | 59 | 6 | 6 | 39 | 86 | 56 | 29 | 7 |
| MAD | 2 | 0 | 0/3 | 63 | 6 | 5 | 27 | >100 | 82 | 48 | 17 |
| MAD | 3 | 33 | 0/3 | 90 | 6 | 2.7 | 11 | 14 | 6 | 9 | 60 |
| Ex. 14 | 5 | 33 | 1/3 | 29 | 6 | 6 | 80 | 57 | 44 | 67 | 0 |
| Ex. 14 | 7.5 | 0 | 0/3 | 61 | 6 | 6 | 16 | 1 | 15 | 15 | 45 |
| Ex. 14 | 10 | 0 | 0/3 | 79 | 3 | 6 | 2 | >100 | 26 | 16 | 45 |
| Ex. 14 + MAD | 5 + 1 | 0 | 0/3 | 93 | 6 | 4.7 | 6 | 9 | 9 | 7 | 66 |
| Ex. 14 + MAD | 7.5 + 1 | 0 | 0/3 | 87 | 3 | 2.3 | 0 | 0 | 0 | 0 | 83 |
| Ex. 14 + MAD | 10 + 1 | 0 | 0/3 | 87 | 0 | 1 | 0 | 0 | 0 | 0 | 89 |
| Ex. 14 + MAD | 5 + 2 | 0 | 0/3 | 86 | 2 | 1.7 | 1 | 0 | 1 | 1 | 85 |
| Ex. 14 + MAD | 7.5 + 2 | 0 | 0/3 | 80 | 4 | 0.7 | 0 | 0 | 0 | 0 | 81 |
| Ex. 14 + MAD | 10 + 2 | 0 | 0/3 | 86 | 2 | 0 | 0 | 0 | 0 | 0 | 87 |
| Ex. 14 + MAD | 5 + 3 | 0 | 0/3 | 92 | 6 | 2 | 0 | 0 | 0 | 0 | 90 |

TABLE 11-continued

Experimental infection with *Eimeria acervulina*, *Eimeria maxima* and *Eimeria tenella* in chicks.
Ex. 14 in combination with Maduramicin.

| Treatment | ppm | mortality % | n | weight % of not inf. control | dropping scores | lesion score | oocyst in % of inf. control |  |  |  | % efficacy tot. |
|---|---|---|---|---|---|---|---|---|---|---|---|
| | | | | | | | ac. | max. | ten. | tot. | |
| Ex. 14 + MAD | 7.5 + 3 | 0 | 0/3 | 89 | 0 | 0 | 0 | 0 | 0 | 0 | 91 |
| Ex. 14 + MAD | 10 + 3 | 66 | 0/3 | 67 | 0 | 0 | 0 | 0 | 0 | 0 | 81 |

TABLE 12

Experimental infection with *Eimeria acervulina*, *Eimeria maxima* and *Eimeria tenella* in chicks.
Ex. 11 in combination with Maduramicin.

| Treatment | ppm | mortality % | n | weight % of not inf. control | dropping scores | lesion score | oocyst in % of inf. control |  |  |  | % efficacy tot. |
|---|---|---|---|---|---|---|---|---|---|---|---|
| | | | | | | | ac. | max. | ten. | tot. | |
| n. inf. contr. | 0 | 0 | 0/6 | 100 | 0 | 0 | 0 | 0 | 0 | 0 | 100 |
| inf. contr. | 0 | 0 | 0/6 | 55 | 6 | 6 | 100 | 100 | 100 | 100 | 0 |
| MAD | 1 | 0 | 0/3 | 59 | 6 | 6 | 39 | 86 | 56 | 29 | 7 |
| MAD | 2 | 0 | 0/3 | 63 | 6 | 5 | 27 | >100 | 82 | 48 | 17 |
| MAD | 3 | 33 | 0/3 | 90 | 6 | 2.7 | 11 | 14 | 6 | 9 | 60 |
| Ex. 11 | 5 | 33 | 1/3 | 42 | 6 | 6 | 19 | >100 | 91 | 47 | 11 |
| Ex. 11 | 7.5 | 0 | 0/3 | 58 | 6 | 6 | 22 | >100 | >100 | 75 | 7 |
| Ex. 11 | 10 | 33 | 1/3 | 41 | 6 | 6 | 91 | 0 | 44 | 72 | 22 |
| Ex. 11 + MAD | 5 + 1 | 0 | 0/3 | 56 | 6 | 2.3 | 15 | 14 | 13 | 14 | 34 |
| Ex. 11 + MAD | 7.5 + 1 | 0 | 0/3 | 63 | 6 | 6 | 5 | 29 | 69 | 28 | 35 |
| Ex. 11 + MAD | 10 + 1 | 0 | 0/3 | 91 | 0 | 4 | 0 | 0 | 0 | 0 | 86 |
| Ex. 11 + MAD | 5 + 2 | 0 | 0/3 | 84 | 4 | 3.5 | 1 | 0 | 0 | 0 | 79 |
| Ex. 11 + MAD | 7.5 + 2 | 0 | 0/3 | 77 | 2 | 2.7 | 2 | 0 | 34 | 12 | 69 |
| Ex. 11 + MAD | 10 + 2 | 0 | 0/3 | 69 | 6 | 0 | 0 | 0 | 0 | 0 | 74 |
| Ex. 11 + MAD | 5 + 3 | 0 | 0/3 | 86 | 1 | 2 | 0 | 0 | 2 | 1 | 85 |
| Ex. 11 + MAD | 7.5 + 3 | 0 | 0/3 | 81 | 0 | 0 | 0 | 0 | 0 | 0 | 91 |
| Ex. 11 + MAD | 10 + 3 | 66 | 0/3 | 64 | 0 | 1 | 0 | 0 | 0 | 0 | 79 |

What is claimed is:

1. A benzimidazole of the formula (I)

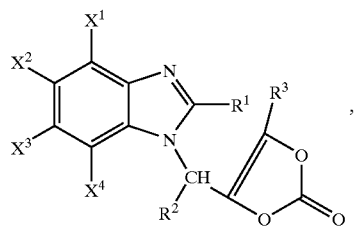

in which

R¹ represents fluoroalkyl,
R² represents hydrogen or alkyl,
R³ represents alkyl,
X¹, X², X³ and X⁴ independently of one another represent hydrogen, halogen, halogenoalkyl, halogenoalkoxy, halogenoalkylthio or halogenoalkylsulfonyl, or alternatively X² and X³ or X³ and X³ together represent a dioxyhaloalkylene.

2. A process for the preparation of compounds as claimed in claim 1 of the formula (I)

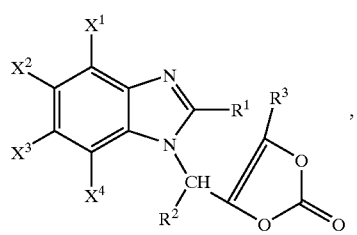

in which

R¹, R², R³, X¹ to X⁴ have the meanings mentioned in claim 1, wherein 1H-benzimidazoles of the formula (II)

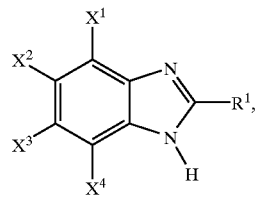

in which

R¹ and X¹ to X⁴ have the meaning indicated in claim 1, are reacted with an alkylating agent of the formula (III)

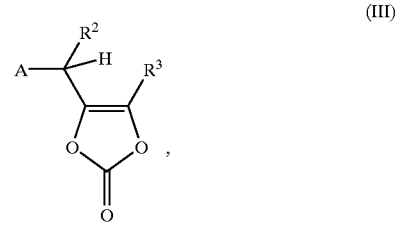

in which

A represents a suitable leaving group,
R² and R³ have the meaning indicated in claim 1.

3. A composition, characterized in that it contains at least one compound of the formula (I) as claimed in claim 1 in combination with extenders and/or surface-active agents.

4. A method for the control of parasites comprising administering to an animal in need thereof an effective amount of a compound of claim 1.

5. A process for controlling parasites comprising administering an effective amount of a compound of claim 1 to said parasites.

6. A process for the preparation of antiparasitics comprising mixing compounds of the formula (I) as claimed in claim 1 with extenders and/or surface-active agents.

* * * * *